(12) United States Patent
Messer et al.

(10) Patent No.: US 7,255,007 B2
(45) Date of Patent: Aug. 14, 2007

(54) CONFIGURATIONS AND METHODS FOR ULTRASOUND TIME OF FLIGHT DIFFRACTION ANALYSIS

(75) Inventors: Barry Messer, Calgary (CA); Matthew Allen Russell Yarmuch, St Albert (CA)

(73) Assignee: Fluor Technologies Corporation, Aliso Viejo, CA (US)

( * ) Notice: Subject to any disclaimer, the term of this patent is extended or adjusted under 35 U.S.C. 154(b) by 0 days.

(21) Appl. No.: 10/541,974

(22) PCT Filed: Jul. 24, 2003

(86) PCT No.: PCT/US03/23369

§ 371 (c)(1),
(2), (4) Date: Feb. 15, 2006

(87) PCT Pub. No.: WO2004/065953

PCT Pub. Date: Aug. 5, 2004

(65) Prior Publication Data

US 2006/0130586 A1    Jun. 22, 2006

Related U.S. Application Data

(60) Provisional application No. 60/440,160, filed on Jan. 14, 2003.

(51) Int. Cl.
G01N 29/04    (2006.01)
(52) U.S. Cl. .......................... 73/622; 73/627; 310/336
(58) Field of Classification Search ................ 73/622, 73/623, 624, 627; 310/334, 336
See application file for complete search history.

(56) References Cited

U.S. PATENT DOCUMENTS

| | | | |
|---|---|---|---|
| 4,326,274 A | 4/1982 | Hotta et al. ................. 367/118 |
| 4,769,571 A | 9/1988 | Habeger, Jr. et al. ........ 310/334 |
| 5,932,807 A | 8/1999 | Mallart ........................ 79/641 |
| 6,105,431 A | 8/2000 | Duffill et al. ................. 73/624 |
| 2002/0078759 A1 | 6/2002 | Bray ........................... 73/763 |

*Primary Examiner*—John E. Chapman
(74) *Attorney, Agent, or Firm*—Fish & Associates, PC

(57) ABSTRACT

An ultrasound test apparatus for polymeric materials (e.g., plastic pipes) includes a low-absorption housing that at least partially encloses an ultrasound transducer, wherein the transducer emits a low frequency wide angle ultrasound beam with a narrow bandwidth. In especially preferred configurations and methods, the apparatus will detect flaws in polymeric pipes, and especially in welds or stressed zones of such pipes, wherein defects of less than 4% of the wall thickness (up to 4 inches) are detected. Further disclosed are configurations and methods for nondestructive detection of lack-of-fusion defects in polymeric pipes.

12 Claims, 4 Drawing Sheets

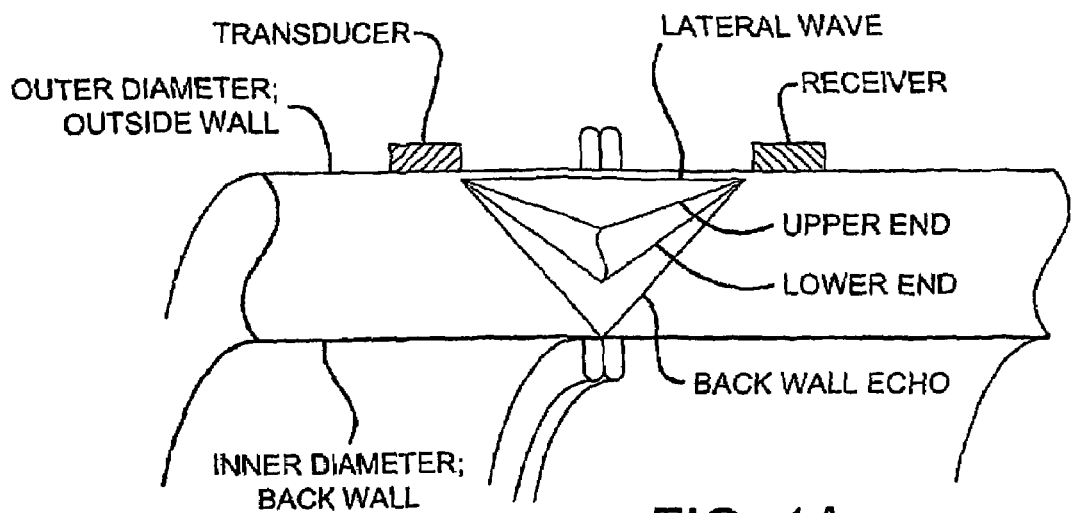
FIG. 1A
FIG. 1B
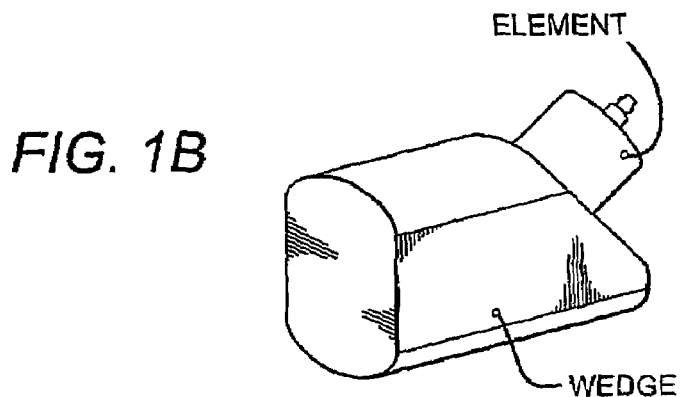
FIG. 1C
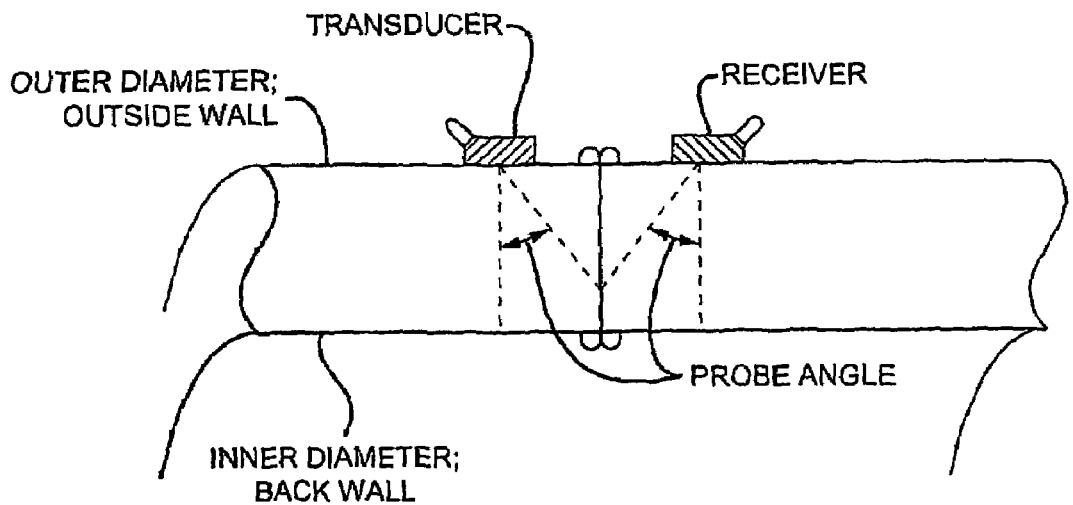

FIG. 1D
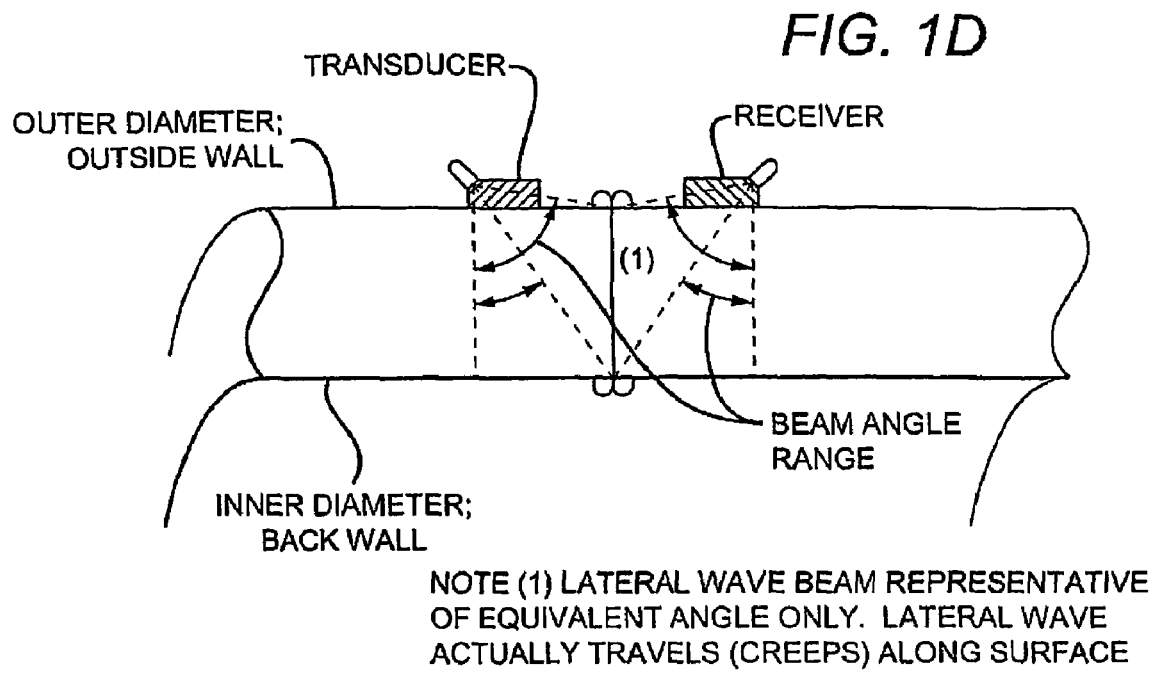
NOTE (1) LATERAL WAVE BEAM REPRESENTATIVE OF EQUIVALENT ANGLE ONLY. LATERAL WAVE ACTUALLY TRAVELS (CREEPS) ALONG SURFACE
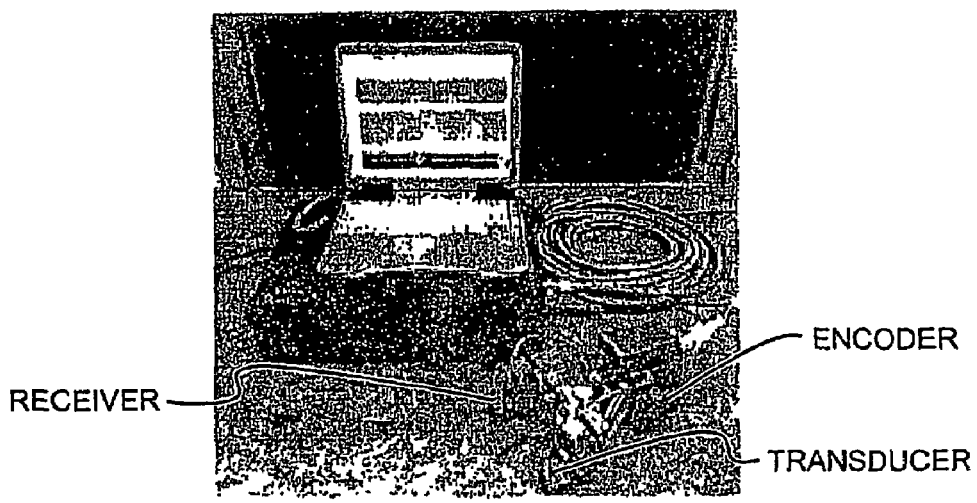
FIG. 2
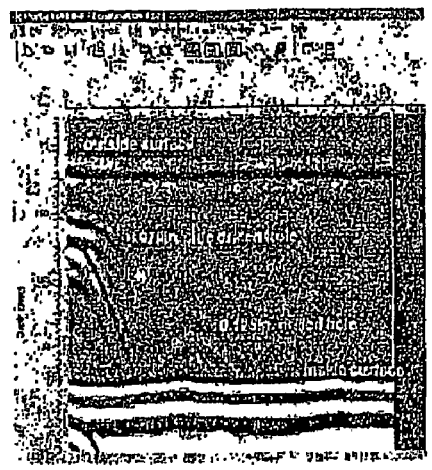
FIG. 3

CONFIGURATIONS AND METHODS FOR ULTRASOUND TIME OF FLIGHT DIFFRACTION ANALYSIS

This application claims the benefit of U.S. provisional patent application with the Ser. No. 60/440,160, filed Jan. 14, 2003, and which is incorporated herein by reference.

FIELD OF THE INVENTION

The field of the invention is non-destructive analysis of materials, and particularly ultrasonic time of flight diffraction analysis of synthetic polymers.

BACKGROUND OF THE INVENTION

Numerous technologies for welding of plastic pipes are known in the art, and depending on the particular pipe requirements or size, various welding methods may be employed. For example, where relatively constant welding temperature is desired, induction welding may be employed. On the other hand, where relatively fast weld and/or cool times are desired, vibration welding may be used. In further applications, where relatively small diameter pipes are welded, electrofusion welding may be employed while butt fusion welding may be especially appropriate for larger diameter pipes.

However, despite the relatively large variety in welding techniques for polymeric materials, validation of the weld quality remains often problematic. Particularly, all or almost all of the known methods for determination of the quality of welds for HDPE (high-density polyethylene) piping exhibit significant problems. For example, the test procedure described in ASTM F600-78 was withdrawn in 1991 because successful inspection techniques as well as subsequent interpretation of the examination results was too dependent on the skill of the operator. Consequently, current industry practice relies in many cases at least in part on visual examination of the exterior weld bead to determine the weld quality. However, field experience frequently shows that there are often substantial inconsistencies between the visual weld bead quality and actual weld integrity.

In another example (e.g., currently known quality control (QC) technique of bend strap tests, as exemplified in ASTM D2657-97), other limitations to ensuring fusion quality are often found. Typically, if a fusion defect is not common to the entire weld, then probability of selecting the defective region of the weld is low. For example, a 30 inch diameter, DR 13.5 (2.22 inch wall) weld has a 3.33 inch sample thickness requirement. Assuming the defect is about 10% of the circumference, then the probability of selecting the defective area is less than 15%. This percentage is further reduced if a random inspection is completed and it is unknown if the weld is defective. Further assuming that about 10% of all welds in the population contain defects, then the probability of finding the defective area of a defective weld is reduced to less than 1.5%.

In still further known methods, ultrasonic testing may be employed in a pulse-echo system to test for various defects in a polymer pipe and/or pipe weld. Ultrasound testing is typically rapid and non-destructive, and relatively inexpensive. However, currently known ultrasound methods are generally limited to relatively thin walls (i.e., less than ¾ inch). Moreover, currently known ultrasonic methods will most likely not detect lack of fusion (LOF) in a butt weld.

To overcome at least some of the disadvantages of visual testing, ultrasonic testing, or random inspection, assembled polymer pipes may be pressurized with a fluid and tested for leakage. However, integrity of a polymer piping system is generally not completely assured using a short-term pressure-leak test (e.g., hydro-tests) due to the viscoelastic nature of the polymer. Whereby, deformational response of the assembled pipe to applied stress depends on both time and material temperature. Therefore, short-term pressure leak tests ensure the absence of leaks in a piping system and are generally not employed to test the strength of plastic piping systems or to ensure long-term life expectancy. Moreover, while some of the recently developed tests improve identification of certain defects at to some extent, all or almost all of such tests need to be performed with non-operational pipelines.

Thus, although there are numerous methods for testing polymer pipes and pipe welds known in the art, all or almost all of them suffer from one or more disadvantages. Still further, most known systems will provide conclusive results only in non-operational pipelines. Therefore, there is still a need to provide improved methods and configurations for testing polymer pipes and pipe welds known in the art, and especially for pipelines that are already in operation.

SUMMARY OF THE INVENTION

The present invention is directed to apparatus and methods of non-destructive testing of polymeric materials, and especially of pipe welds and pipes fabricated from thermoplastic polymers. Contemplated devices will generally include a low-absorption housing that at least partially encloses an ultrasound transducer, wherein the transducer emits a low frequency and wide angle ultrasound beam having a narrow bandwidth. Contemplated devices may further include an ultrasound receiver in pitch-catch arrangement with the transducer, preferably having a beam angle of about 40 degrees and about 70 degrees. The table below summarizes generally contemplated and especially preferred values/ranges for exemplary devices according to the inventive subject matter.

|  | TYPICAL RANGES/ VALUES | PREFERRED ASPECT |
| --- | --- | --- |
| Frequency | 1 to 5 MHz | 2.25 MHz |
| Bandwidth | 5 to 50% | ±10% |
| Probe Angle | 45 to 75° | 60° |
| Beam Angle | 30° to 80° | 40° to 70° |

In one aspect of the inventive subject matter, it is preferred that the low-absorption housing comprises high-impact polystyrene, and/or that the bandwidth of the transducer may vary considerably. However, transducers having a bandwidth between 5% and 50% of signal frequency, and more preferably a bandwidth of about ±10% of the nominal frequency of the transmitter are particularly preferred. In especially preferred aspects, the housing comprises a high-impact polystyrene, and the ultrasound frequency is about 2.25 MHz at a bandwidth of about ±10%.

In another aspect of the inventive subject matter, contemplated devices further include an ultrasonic receiver in pitch-catch arrangement with the transducer, wherein the ultrasonic receiver produces a signal that is preferably processed using a signal processing software that translates the signal into a visual output.

Consequently, the inventors contemplate methods of use and/or marketing of an ultrasound test apparatus in which in one step an apparatus is provided that has a low-absorption housing at least partially enclosing an ultrasound transducer, wherein the transducer emits a low frequency wide angle ultrasound beam having a bandwidth of 5 to 50% of the nominal transmitter frequency. In another step, information is provided that the apparatus is useful in detection of a flaw (e.g., inclusion, lack of fusion, and/or fracture) in a polymeric material. With respect to the apparatus, the same considerations as described above and in the section entitled "Detailed Description" below apply.

In further preferred aspects, the information in contemplated methods may further include advice that the lack of fusion is detected by a loss of at least one of a back wall echo and/or a lateral wave, and/or advice that the apparatus will detect a flaw in the polymeric material (e.g., flaw size less than 4% of the thickness of the polymeric material), when the polymeric material has a thickness of up to 4 inches.

BRIEF DESCRIPTION OF THE DRAWING

FIG. 1A is a schematic of an exemplary apparatus according to the inventive subject matter in contact with a plastic pipe having a butt weld.

FIG. 1B is a schematic of an exemplary transducer of the apparatus of FIG. 1A.

FIG. 1C is a schematic of an exemplary probe angle according to the inventive subject matter.

FIG. 1D is a schematic of an exemplary beam angle range according to the inventive subject matter.

FIG. 2 is a photograph of an exemplary UT-TOFD test system according to the inventive subject matter.

FIG. 3 is a screen copy of a graphical representation of an exemplary UT-TOFD test calibration according to the inventive subject matter.

DETAILED DESCRIPTION

Figure 4A:
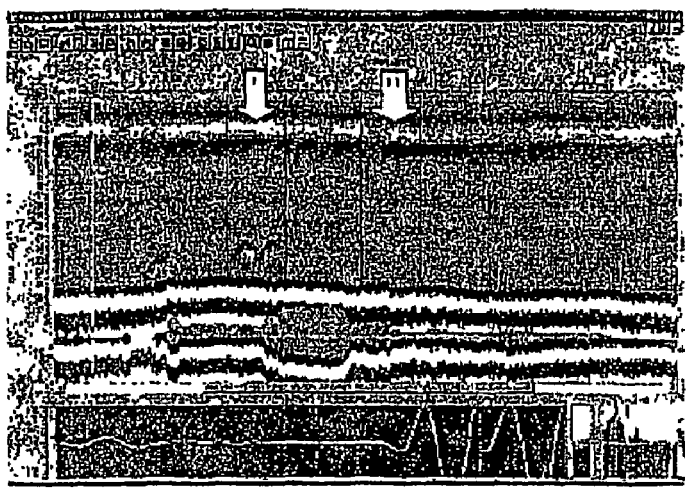
FIG. 4A is a screen copy of a graphical representation of an exemplary UT-TOFD scan of Weld A of an HDPE pipe in a first location.

The inventors discovered that polymeric pipes and pipe welds can be examined with high accuracy and at large wall thickness using a modified UT-TOFD (Ultrasonic Time-of-Flight Diffraction) system. In a particularly preferred aspect of the inventive subject matter a modified probe is employed in conjunction with high-resolution/high-sensitivity software to detect, locate and determine the defect type, including porosity and lack of fusion, and size in high-density polyethylene pipe welds.

The inventors further discovered that configurations and methods according to the inventive subject matter are capable of detecting defects of less than 4% of wall thickness in a pipe with a thickness of up to 4 inches. Moreover it should be particularly appreciated that the type, size, and/or location of defects discovered using contemplated methods and configurations correlate well with findings from destructive examination of the same pipe and/or pipe butt weld.

In an exemplary UT-TOFD system according to the inventive subject matter as shown in FIG. 1A, transducer and receiver are arranged in a pitch-catch arrangement to simultaneously send and detect compression waves in the inspection area. The inspection area boundaries are defined by the lateral wave signal that is directed just below the surface (outer diameter, OD), and the back-wall echo signal that is directed at the back wall or pipe inner diameter (inner diameter, ID). The TOFD method generally measures the arrival times (time of flight) of the various signals, while the analysis software automatically performs Pythagorean calculations required to accurately locate (by circumferential position and depth) and size (i.e., length, height) defects. Signals from any flaws in the inspection area will appear in a graphical representation (e.g., oscilloscope wave or visual representation of scanned area) between the lateral wave signal and the back-wall signal.

An actual exemplary device is depicted in FIG. 2 where the device includes a transducer and an ultrasound receiver that are both coupled to an encoder to provide positional information. The device is further coupled via a cable to a portable computer that executes a program calculating and displaying signals from the ultrasound receiver to provide positional information of a flaw in a weld as well as size information of the flaw.

Previously known UT-TOFD methods and configurations were generally limited to flaw detection in polymeric materials having a thickness of less than ¾ inch, and due to the relatively poor signal-to-noise ratio, resolution was often less than satisfactory. Moreover, LOF defects were typically not detectable with such configuration and methods. In contrast, the inventors discovered that all or almost all of such deficiencies can be remedied if the UT-TOFD system had a configuration in which a low-absorption housing at least partially enclosed an ultrasound transducer that emits a low frequency wide angle ultrasound beam having a narrow bandwidth, typically at a beam angle of between about 40 degrees and about 70 degrees.

As used herein, the term "polymeric materials" generally refers to synthetic materials in which a plurality of repeating units form a chain or three-dimensional network, and especially contemplated polymeric materials include thermoplastic materials (e.g., high-density polyethylene, polypropylene, polyamide, or polyvinylidene fluoride). Moreover, composite materials (e.g., with metals, carbon, fiber glass, or other polymeric materials) that include polymeric materials are also considered to be within the scope of this definition.

As also used herein, the term "low-absorption housing" refers to a housing that (a) at least partially includes an ultrasound source (e.g., piezo-electric transducer), and (b) exhibits no more than about 25%, more typically no more than about 10% of the absorption of ultrasound energy of the ultrasound source as compared to a housing fabricated from high-impact polystyrene (e.g., STYRON™ or STYRON A-TECH™, commercially available from Dow Chemicals). Most typically, however, suitable housings will absorb ultrasound energy similarly or even less than a housing fabricated from high-impact polystyrene. The housing may further include an ultrasound insulator that contacts at least part of the ultrasound source. Further particularly preferred low-absorption housings may also be formed from or comprise LEXAN (High-impact polycarbonate, commercially available from General Electrics). Where the term "about" is used in conjunction with a numeral, it should be understood that the numeral may exhibit a positive or negative variation of no more than 10%, inclusive. For example, the term "about 10%" refers to a range of 9.0% to 11.0%, inclusive.

As further used herein, the term "frequency between about 0.5 MHz and 10 MHz ultrasound transducer" refers to any ultrasound source, and particularly those that produce a beam of ultrasound energy having a frequency between about 0.5 MHz and 10 MHz. Therefore, contemplated ultrasound transducers will especially include piezo-electric ultrasound transducers, laser-driven ultrasound generators, and electromagnetic ultrasound transducers. Consequently, the term "low frequency" as used herein refers to a frequency between about 0.5 MHz and 10 MHz, more preferably between about 1.0 MHz and 4.0 MHz, and most preferably between about 2.0 MHz and 2.5 MHz.

As still further used herein, the term "wide angle ultrasound beam" generally refers to any ultrasound beam that will have an angle sufficient to simultaneously provide ultrasound energy to both surfaces of the material to be tested. Therefore, a wide angle ultrasound beam will produce a lateral wave traveling substantially parallel to the surface that is contacted by the ultrasound transducer and a sound wave impinging on the back wall (the surface that is opposite to the surface that is contacted by the ultrasound transducer; see also FIG. 1A). Typically, the wide angle of the ultrasound beam will be between about 30-80 degrees, and more typically between about 40-70 degrees. Similarly, the term "beam angle" as used herein refers to the impact angle of the ultrasound beam relative to an axis normal to the surface that is contacted by the ultrasound transducer; see also FIG. 1D.

As also used herein, the term "narrow bandwidth" refers to a bandwidth of about ±25% of the nominal frequency of the transducer, more typically ±15% of the nominal frequency of the transducer, and most typically about ±10% of the nominal frequency of the transducer.

In one preferred aspect of the inventive subject matter, the inventors discovered that the signal strength that is received by an ultrasound receiver in pitch-catch arrangement with an ultrasound transducer can be significantly improved over conventional and known TOFD systems by disposing the transducer in a housing that is fabricated from high impact resistant polystyrene. Of course, it should be recognized that various materials other than high impact resistant polystyrene are also contemplated, so long as such materials have a lower absorption of the ultrasound energy as compared to previously known housing materials (Ultrasound absorption of a material can easily be determined by a person of ordinary skill in the art, for example, by using a conventional ultrasound test system in pulse-echo configuration with various materials).

Thus, suitable alternative materials for contemplated housings will include various synthetic high impact resistant polymers (e.g., high-impact resistant polyurethane, high-impact resistant polycarbonate, etc.), metals, metal alloys, and any reasonable combination thereof. While not wishing to be bound by a particular theory, the inventors contemplate that preferred housings will allow formation of a more focused ultrasound beam and/or significantly improve acoustical match to enhance sensitivity. Consequently, it is also contemplated that suitable housings may further include an acoustic insulator and/or dampening material that isolates the transducer from the housing.

With respect to the transducer, it is generally preferred that the transducer will emit a wide angle ultrasound beam, and particularly preferred probe angles are generally between about 55 degrees and 65 degrees, and most preferably at about 60 degrees; see also FIG. 1C. It is also contemplated that the bandwidth of the transducer may vary considerably. Typically, suitable transducers may have a bandwidth of between about 5% and 50% of the nominal frequency. However, transducers having a relatively narrow bandwidth (typically about +/−10% of the nominal frequency [e.g., 2.25 MHz +/−10%]) are especially preferred to maximize sensitivity and resolution. Among other advantages, it is contemplated that a narrow bandwidth will provide a significantly higher signal output at the center frequency as compared to broader bandwidth transducers, which may result in increased signal penetration. Thus, it should be recognized that the narrow bandwidth together with the wide beam advantageously allows for a high-resolution response. Preferred frequencies of the transducer are generally in the low range and will typically lie between about 1 MHz and about 5 MHz. However, an especially preferred frequency is about 2.25 MHz. Thus, particularly suitable transducers may include a standard lead zirconate titanate (PZT) compound crystal that is embedded in/filled with a polymer, and an exemplary transducer is depicted in FIG. 1B.

In a particularly preferred configuration in which the housing of the transducer was fabricated from high impact resistant polystyrene, and in which the transducer had a frequency of 2.25 MHz at a probe angle of 60 degrees with a narrow band width, the inventors discovered that the signal that is obtained is substantially stronger than signals obtained using conventional TOFD configurations. Moreover, when the signal was processed using third generation imaging software (e.g., commercially available from RTD Quality Services, Inc., Delftweg 144, 3046 NC Rotterdam, The Netherlands), signals obtained were an order of magnitude stronger than signals obtainable using conventional TOFD configurations. With respect to the transducer dimensions, it should be appreciated that all sizes and configurations are suitable. However, smaller transducers are generally preferred and will have a contact diameter of about 1⁄2 inch.

Based on their observations, the inventors contemplate that since the transducer signals are compression waves with the same velocity as diffracted signals, the depth of all sources of flaw signals can be calculated from the arrival times of the signals using Pythagorean theorem calculations, which are performed automatically by the TOFD system. Therefore, particularly preferred software will measure arrival times of signals (time of flight) and provide an algorithm for Pythagorean calculations to determine flaw location and instant visualization of flaw indicators. Depending on the particular material tested and configuration employed, it should be recognized that the software can also provide a visual representation of the signals received from the ultrasound receiver. Consequently, it should be appreciated that the software in combination with contemplated systems will not only significantly improve resolution and detection capabilities (e.g., flaw dimension and orientation) in materials with thickness of greater than 3⁄4 inch, but also provides potential identification of a flaw type.

For example, the inventors further discovered that a "disruption" or "loss" of the lateral wave and/or back wall echo may also serve as an indication of serious fusion flaws, and are especially indicative for lack of fusion flaws. In another example, diffracting ultrasonic signals are shown as TOFD indicators on the inspection image, for example as points reflectors, indicating the position (circumferential, depth) and size (length, height) of potential flaws. This allows for a quantitative engineering analysis of actual flaws that exist within fusion butt welds. Therefore, it should be recognized that contemplated systems and methods are particularly useful for advanced fracture mechanics analysis to determine weld integrity and any future pipeline operational risks. Still further, it should be recognized that contemplated systems may even be employed in operating pipe lines.

Experiments and Data

The following data and experiments are provided to present a person of ordinary skill in the art with exemplary guidance for using a UT-TOFD device as described above in combination with commercially available software (e.g. Pythagorean signal analysis and visualization from RTD, Inc.).

Calibration of UT-TOFD

HDPE pipes with artificial defects were employed in various experiments to provide calibration for contemplated systems. The weld information was obtained in a circumferential scan around the pipe surface using a UT-TOFD device with an encoder for providing positional information of the acquired ultrasound signals. As shown in FIG. 3, the TOFD display appears as a cross-sectional "side-view" of the weld zone. Any weld flaws are displayed as a series of black and white lines (phases), located at the accurate location and depth in the weld material. The inventors determined in various calibration experiments that the maximum specimen thickness for inspection was up to and including 3.875 inches of wall thickness with a probe nominal frequency of 2.25 MHz. Based on the diffracted signal from reference diffractors, and as shown in FIG. 3, UT-TOFD according to the inventive subject matter accurately located and sized manufactured flaws for a 2.5 inches thick specimen. Calibration for other samples also provided positive correlation to reference diffractors.

The probe separation was determined by completing a geometrical analysis of the system and inspection area. The following factors were taken into account: Pipe diameter and DR rating, probe crystal beam width diameter 0.5 inch, and the incidence beam angle 40-70° and probe angle of 60°±5°. The probe separation shown in Table 1 below provided typical coverage for the entire thickness of the weld inspection region.

TABLE 1

| Pipe Wall Thickness | Probe Angle and Frequency | Probe Separation |
| --- | --- | --- |
| ≦0.85" | 60° ± 5°- 2.25 Mhz | 1.5" ± 0.5" |
| 0.85 to 1.5" | 60° ± 5°- 2.25 Mhz | 2.7" ± 0.5" |
| 1.5" to 2.5" | 60° ± 5°- 2.25 Mhz | 4.7" ± 0.5" |
| 2.5" to 4" | 60° ± 5°- 2.25 Mhz | 6.9" ± 1.0" |

Supplementary calibration tests were completed to verify that the technique could be utilized on a live, operating pipeline system. Completing calibration scans while the pipe ID was immersed in both stagnant and flowing water facilitated modeling of actual operating conditions. It was found that the system provided exceptional resolution results and accurately located manufactured flaws. In exemplary systems, the inventors determined that the minimum detected flaw size is approximately 4% of wall thickness of a plastic pipe for various ranges of pipe sizes tested. Furthermore, the inventors determined that the sensitivity and/or signal resolution were not a function of position of the defect. The signal-to-noise ratio in most of the calibration experiments was approximately ≧6 dB.

Tests on Actual Welds and Independent Validation

Field welds were visually inspected by a qualified third-party inspection agency. Subsequently, a two-person UT-TOFD crew examined the field welds. With 15 minutes per field weld, the crew set up, inspected, and categorized defects in butt welds. A total of 132 field welds were UT-TOFD examined using contemplated systems, with pipe sizes ranging from 22 inches to 32 inches and wall thickness range of 0.846 inch to 3.333 inches. At the pipeline site, UT-TOFD scans detected welds that contained suspected severe fusion defects. To ensure that the suspected defects were actual defects, the team removed two suspect welds from the pipeline and labeled them Weld A and Weld B. Samples were then prepared for destructive examination (DE) and characterization of fusion defects followed by correlation of the UT-TOFD and DE results. All welds were butt welds of HDPE plastic pipe of the type PE3408.

Figure 4B:
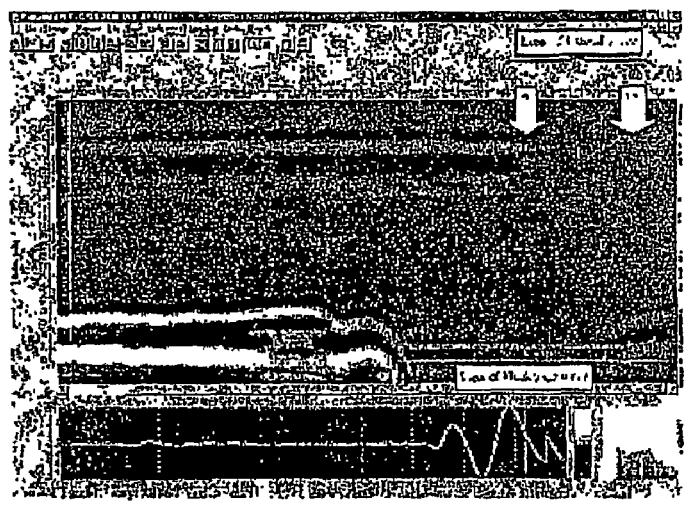
FIG. 4B is a screen copy of a graphical representation of an exemplary UT-TOFD scan on Weld A of a HDPE pipe in a second location.

UT-TOFD Detected Fusion Flaws—Weld A:

The UT-TOFD scan for Weld A, samples 1 and 1.1 is shown in FIG. 4A. As can be clearly seen, the UT-TOFD scan for Weld A, sample 1, contained two distinct point reflectors but no loss of back wall wave, while sample 1.1 was "clear" of indications. Weld fusion was expected to be good in samples 1 and 1.1 of Weld A. In contrast, as depicted in FIG. 4B, the UT-TOFD scan for Weld A, samples 2 and 2.1 includes a loss of back wall echo and a loss of the lateral wave, indicating areas of lack of fusion.

Destructive Examination of Fusion Defects—Weld A

The destructive examination of previously UT-TOFD analyzed specimen provided the following analysis summarized in Table 2 below. Each sample was tested and failure mode determined, which is accompanied by test observations and remarks for the respective samples.

TABLE 2

| Sample (A) | Failure Mode | Bend Test Observations and Remarks |
| --- | --- | --- |
| 1 | Ductile Overload | Failure near, but not on the weld interface. Dull fibrous fracture face and shear lips from final specimen failure |
| 1.1 | Ductile Overload | Failure near, but not on the weld interface. Dull fibrous fracture face and shear lips present from final fracture |
| 2 | Brittle Fracture | Failure on the weld interface. Brittle fracture face constant along entire through-thickness |
| 2.1 | Brittle at onset and ductile final fracture | Brittle fracture during onset of fracture on weld interface. Ductile fracture mode during final fracture |

Correlation Between UT-TOFD and Destructive Examination—Weld A

Table 3 summarizes findings determined for Weld A by both non-destructive UT-TOFD and destructive examination. As can be clearly taken from the results, UT-TOFD results correlated well with the findings from the destructive examination, wherein point reflectors were likely indicators of localized defects (e.g., inclusions, or weld porosity) and wherein lack of back wall echo and/or loss of lateral wave were likely indicators of gross defects, and particularly lack of fusion.

TABLE 3

| SAMPLE (A) | UT-TOFD | DESTRUCTIVE EXAMINATION |
|---|---|---|
| 1 | 2 isolated point reflectors | Failed via ductile overload |
| 1.1 | No indication | No fracture along weld interface, and exhibited ductile fracture surface |
| 2 | Areas with loss of back wall wave and lateral wave | Sample exhibited brittle fracture surface characteristic of poor bonding (associated with lack of fusion) |
| 2.1 | Complete loss of back wall and lateral wave | Failure initiated via brittle fracture, but final fracture was by ductile mechanisms |

UT-TOFD Detected Fusion Flaws—Weld B

Figure 5:
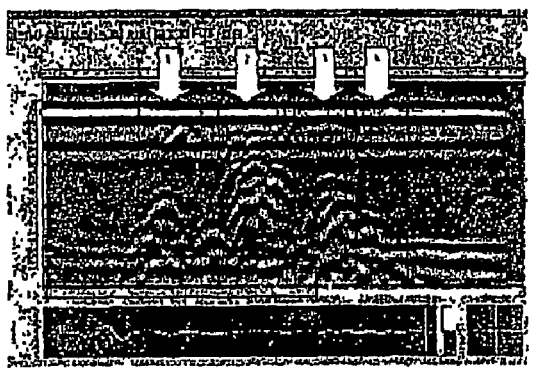
FIG. 5 is a screen copy of a graphical representation of an exemplary UT-TOFD scan on Weld B of a HDPE pipe.

Similar tests as described above for Weld A were performed on Weld B with the following results. The UT-TOFD scan of Weld B as depicted in FIG. 5 revealed the presence of multiple point reflectors, coupled with an interruption of the back wall echo, which indicated severe lack of fusion, "cold weld" conditions, and weld porosity.

Destructive Examination of Fusion Defects—Weld B

The destructive examination of the previously UT-TOFD analyzed specimen provided the following analysis for the points indicated as summarized in Table 4 below. Again, each sample was tested and failure mode determined, which is accompanied by test observations and remarks for the respective samples.

TABLE 4

| SAMPLE (A) | FAILURE MODE | BEND TEST OBSERVATIONS AND REMARKS |
|---|---|---|
| 1 | Brittle Fracture | Failure on the weld interface without appreciable gross plastic deformation. The flat fracture face indicates brittle fracture |
| 2 | Ductile fracture | Failure not entirely on the weld interface. Dull fibrous fracture face and shear lips present from final fracture. The presence of pores resulting from poor fusion is confirmed on fracture face |
| 3 | Brittle Fracture | Brittle fracture face on the weld interface and weld failure |
| 4 | Brittle Fracture | Brittle fracture along weld interface and weld failure |

Correlation Between UT-TOFD and Destructive Examination—Weld B

Table 5 summarizes findings determined for Weld B by both non-destructive UT-TOFD and destructive examination. As can be clearly taken from the results, UT-TOFD results correlated well with the findings from the destructive examination, wherein point reflectors were likely indicators of localized defects (e.g., inclusions, or weld porosity) and wherein lack of back wall echo and/or loss of lateral wave were likely indicators of gross defects, and particularly lack of fusion.

TABLE 5

| SAMPLE (A) | UT-TOFD | DESTRUCTIVE EXAMINATION |
|---|---|---|
| 1 | Multiple point reflectors (bottom to top) | Brittle fracture with porosity |
| 2 | Multiple point reflectors, disruption of back wall wave | Ductile fracture with excessive porosity |
| 3 | Multiple point reflectors | Brittle fracture with porosity |
| 4 | Multiple point reflectors, disruption of back wall wave | Brittle fracture with excessive porosity |

The results from Weld A positively verify that an interruption of the back wall echo and/or lateral wave is correlated to severe lack of fusion (cold weld) conditions. While not wishing to be bound by a particular theory of hypothesis, the inventors contemplate that the loss of lateral wave and or back wall echo is indicative for a situation where ultrasonic energy can not readily travel through the weld interface. Thus, once the ultrasound is scattered in the weld interface, reflections/diffractions can not be picked up anymore by the receiver. Consequently, absence of reflections/diffractions signals (to be picked up by the receiver) indicates non-homogeneity in the weld zone, which is indicative of LOF (lack of fusion) conditions. As was observed by the destructive examination, it should be especially appreciated that a LOF region can be identified with relatively high accuracy using contemplated methods and apparatus.

The results of Weld A, Samples 1 and 1.1, also confirm that a "clear" UT-TOFD scan is free of fusion defects and that isolated point reflectors may not be critical enough to induce weld zone failure during bend tests. Isolated point reflectors are therefore not always regarded as a concern for determining weld integrity. In contrast, as verified in Weld B multiple point reflectors with close proximity to each other will pose clear cause for concern.

Furthermore, the significant disruption of the back wall and lateral wave signals in Weld B also indicates severe lack of fusion conditions of the pipe ends. Complete joining of pipe ends to ensure homogenous material properties across the fusion zone is an underlying assumption of proper fusion conditions. A change in material properties at the weld interface results in a disruption of ultrasonic signals, and it should be recognized that UT-TOFD images produced using contemplated methods and configurations correlate to changes in properties by reflection and/or diffraction at the weld interface. The samples established conclusively that UT-TOFD is sufficiently sensitive to identify LOF (cold weld) anomalies.

In Weld B, Sample 2, the inventors concluded that the observed weld failure via a ductile mechanism, in lieu of brittle fracture common to adjoining material, could be the result of how the cold weld was formed. For example, when a weld bevel cools significantly, a crystalline skin can form that does not permit proper fusion. It is possible that this local area in Weld B, sample 2, was not cooled to the same degree as the adjacent samples. However, excessive weld porosity that was positively identified and correlated for Sample 2, are adequate grounds for rejection of the entire weld.

For all samples, the excellent correlation between flaw indications (e.g. point reflectors) and actual fusion defects (e.g. porosity) further verifies the sensitivity level of UT-TOFD inspection method. In addition, the presence of multiple point reflectors is a secondary indicator of possible lack of fusion conditions. It is also clear that the presence of multiple point reflectors, coupled with an interruption of the back wall and/or lateral wave within the same area of a weld positively identifies an area of extremely poor fusion.

Interestingly, of a 132 weld population, a very large "gray zone" including welds with marginally poor or marginally acceptable visual external welds beads did not correlate to the weld integrity as determined by UT-TOFD scans. Of these welds, 19% deemed visually acceptable by project specifications were subsequently found to contain various UT-TOFD flaw indications, with many indicating severe fusion defects. In contrast, 63% of the welds identified as being visually unacceptable were found to be clear of any serious flaw indications.

Further Findings on Other Welds

Figure 6:
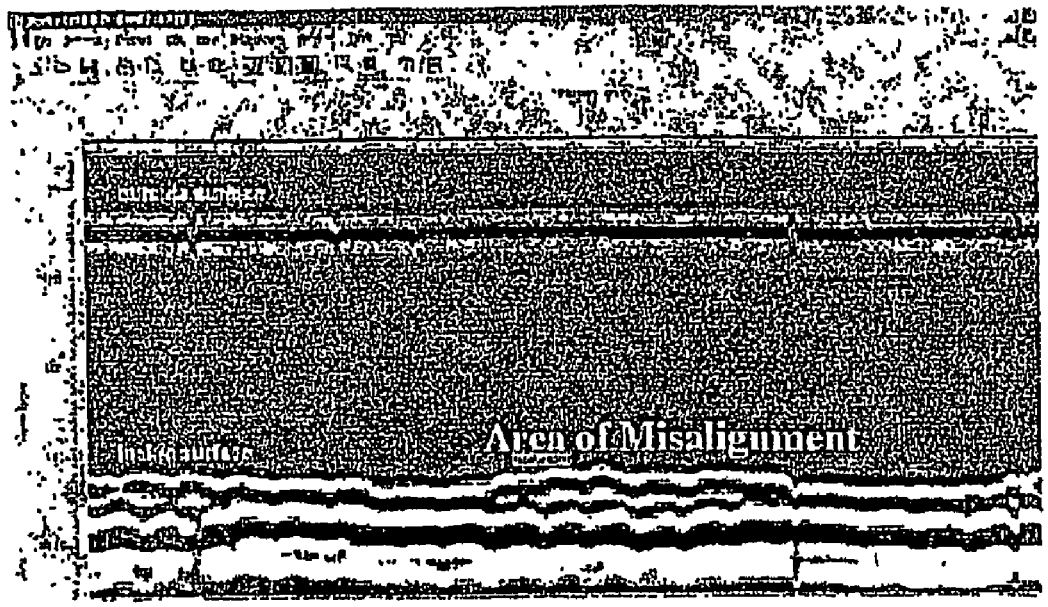
FIG. 6 is a screen copy of a graphical representation of an exemplary UT-TOFD scan on a weld of a HDPE pipe with a misalignment.
Figure 7:
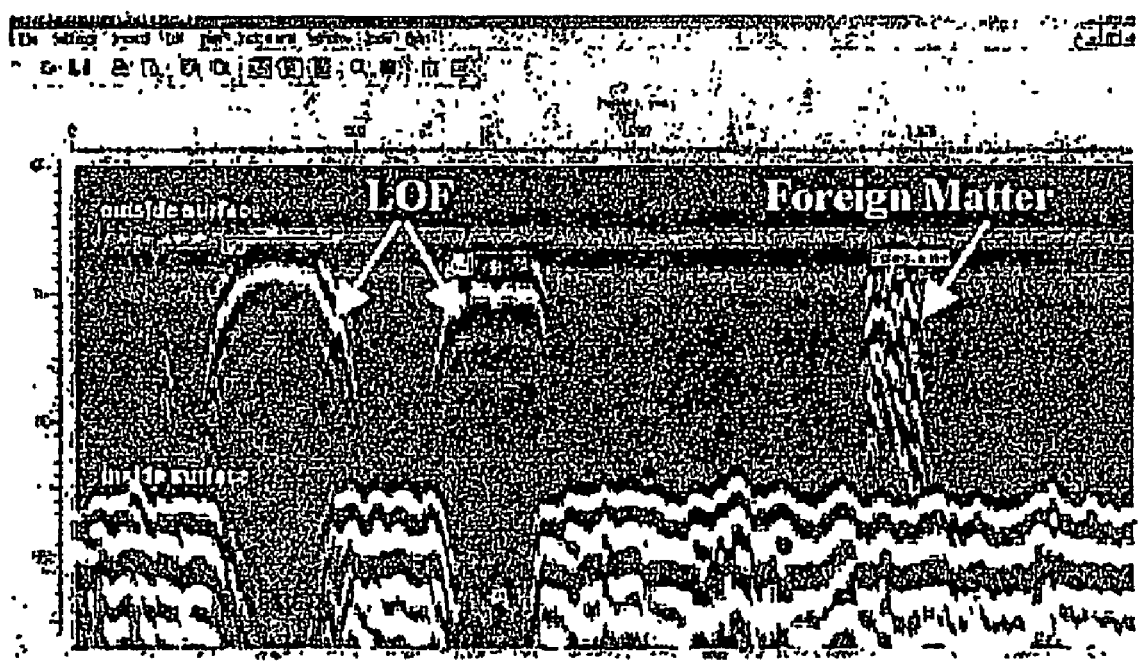
FIG. 7 is a screen copy of a graphical representation of an exemplary UT-TOFD scan on a weld of a HDPE pipe with lack of fusion defects and inclusion of foreign matter.

The inventors still further discovered that misalignment of two pipe segments may be detected via indication of a change in the phase of the back wall echo and/or lateral wave as depicted in FIG. 6. Here, the change in the black-and-white alternating pattern is clearly reversed throughout the area of misalignment. FIG. 7 depicts a UT-TOFD scan of a pipe weld that includes foreign matter in an area next to areas with gross fusion defects (lack of fusion).

Based on these and other findings (data not shown), the inventors contemplate that the methods and apparatus according to the inventive subject matter may be employed for on-site testing of a live pipeline (among other advantages, use of a relatively low frequency [e.g., 2.25 MHz] will generally allow data generation/acquisition that is free or almost free of interference from pipeline contents). Alternatively, or additionally, the inventors contemplate that such methods and apparatus may be useful for risk assessment of existing or suspected defects (e.g., to help decide if replacement or repair is advised) and for performing analysis to calculate crack propagation susceptibility. In still further aspects, it should be recognized that contemplated methods and apparatus may be useful for verification of existing plastic butt weld fusion parameters, techniques and equipment, if correct temperature, pressure, and time combinations are utilized for fusion of HDPE butt welds.

Consequently the inventors contemplate a methods of use and/or marketing of an ultrasound test apparatus in which in one step an apparatus is provided that has a low-absorption housing at least partially enclosing an ultrasound transducer, wherein the transducer emits a low frequency wide angle ultrasound-beam having a narrow bandwidth. In another step, information is provided that the apparatus is useful in detection of a flaw (e.g., inclusion, lack of fusion, and/or fracture) in a polymeric material.

Thus, specific embodiments and applications of UT-TOFD have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. Moreover, in interpreting the specification, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. An ultrasonic test apparatus for polymeric materials comprising a low-absorption housing at least partially enclosing an ultrasound transducer that emits a low frequency wide angle ultrasound beam having a narrow bandwidth.

2. The apparatus of claim 1 wherein the low-absorption housing comprises high-impact polystyrene.

3. The apparatus of claim 1 wherein the low frequency is between about 1 MHz and about 5 MHz.

4. The apparatus of claim 1 wherein the ultrasound beam is emitted at a beam angle of between about 30 degrees and about 80 degrees.

5. The apparatus of claim 1 wherein the bandwidth is about ±10% of the low frequency.

6. The apparatus of claim 1 wherein the housing comprises high-impact polystyrene, and wherein the low frequency is about 2.25 MHz at a bandwidth of about 10%.

7. The apparatus of claim 6 wherein the ultrasound beam is emitted at a probe angle between about 30 and about 80 degrees.

8. The apparatus of claim 1 wherein the polymeric material comprises a high impact resistant polystyrene.

9. The apparatus of claim 1 wherein the polymeric material is selected from the group consisting of high-density polyethylene, polypropylene, and polyvinylidene fluoride.

10. The apparatus of claim 1 further comprising an ultrasound receiver in pitch-catch arrangement with the transducer, wherein the ultrasound receiver produces a signal.

11. The apparatus of claim 10 wherein the signal is processed using a signal processing software that translates the signal into a visual output.

12. The apparatus of claim 11 wherein the visual output is displayed on a portable device that is electronically coupled to at least one of the transducer and ultrasound receiver.

* * * * *